(12) United States Patent
Goede et al.

(10) Patent No.: US 10,107,739 B2
(45) Date of Patent: Oct. 23, 2018

(54) SYSTEM AND METHOD FOR CONFOCAL RAMAN-SPECTROSCOPIC MEASUREMENTS OF BIOLOGICAL SAMPLES

(71) Applicant: UNCHAINED LABS, Pleasanton, CA (US)

(72) Inventors: Karsten Goede, Berlin (DE); Lothar Holz, Berlin (DE); Markus Lankers, Schoneiche (DE); Oliver K. Valet, Berlin (DE)

(73) Assignee: UNCHAINED LABS, Pleasanton, CA (US)

( * ) Notice: Subject to any disclaimer, the term of this patent is extended or adjusted under 35 U.S.C. 154(b) by 0 days.

(21) Appl. No.: 15/379,546

(22) Filed: Dec. 15, 2016

(65) Prior Publication Data

US 2017/0176320 A1    Jun. 22, 2017

(30) Foreign Application Priority Data

Dec. 16, 2015  (EP) .................................... 15200489

(51) Int. Cl.
*G01N 21/03* (2006.01)
*G01N 33/483* (2006.01)
*G01N 21/65* (2006.01)

(52) U.S. Cl.
CPC ............ *G01N 21/03* (2013.01); *G01N 21/65* (2013.01); *G01N 33/483* (2013.01);
(Continued)

(58) Field of Classification Search
CPC ............................. G01N 21/03; G01N 21/65
See application file for complete search history.

(56) References Cited

U.S. PATENT DOCUMENTS

2004/0019283 A1*  1/2004  Lambert ............ A61B 5/14532
                                                  600/476
2005/0095696 A9*  5/2005  Lemmo ................ B01J 19/0046
                                                  435/287.1

(Continued)

FOREIGN PATENT DOCUMENTS

DE      103 44 784      4/2005
WO      2011/148407     12/2011

OTHER PUBLICATIONS

Koch Hanna et al: "Design and validation of a multimodal low-budget Raman microscope for liquid and solid phase applications", Optomechatronic Micro/Nano Devices and Components III: Oct. 8-10, 2007, Lausanne, Switzerland; [Proceedings of SPIE, ISSN 0277-786X], SPIE, Bellingham, Wash, vol. 9529, May 19, 2015 (May 19, 2015), pp. 952917-952917.

(Continued)

*Primary Examiner* — Shawn Decenzo
(74) *Attorney, Agent, or Firm* — Cooley LLP

(57) ABSTRACT

Disclosed herein is a system, particularly a microscope system, for confocal Raman-spectroscopic measurements. The system is configured to detect minute sample amounts of microbes in a sample chamber with a lid, wherein the system is configured such that a comparably large working distance between the objective lens and the sample is sustained such that a measurement can be performed through the lid of the sample chamber. This allows for cultivating and measuring the sample in the same container.

14 Claims, 2 Drawing Sheets

(52) U.S. Cl.
CPC ............... *G01N 2021/0385* (2013.01); *G01N 2201/0846* (2013.01); *G01N 2201/10* (2013.01)

(56) References Cited

U.S. PATENT DOCUMENTS

| | | |
|---|---|---|
| 2006/0135861 A1 | 6/2006 | Lucassen et al. |
| 2010/0241357 A1* | 9/2010 | Chan .................... G01J 3/44 702/19 |
| 2010/0284016 A1 | 11/2010 | Teitell et al. |

OTHER PUBLICATIONS

H E Keller: "Objective Lenses for Confocal Microscopy" In: "Handbook of Biological Confocal Microscopy, Third Edition", Jan. 1, 2006 (Jan. 1, 2006), Springer Science + Business Media, XP055280861, ISBN: 978-0-387-45524-2, pp. 145-161.

* cited by examiner

Prior Art

SYSTEM AND METHOD FOR CONFOCAL RAMAN-SPECTROSCOPIC MEASUREMENTS OF BIOLOGICAL SAMPLES

CROSS REFERENCE TO RELATED APPLICATIONS

Benefit is claimed to European Patent Application No. EP15200489.1, filed Dec. 16, 2015, the contents of which are incorporated by reference herein in their entirety.

FIELD

The invention relates to a system and a method for confocal Raman-spectroscopic measurements of biological samples, such as for example prokaryotic or eukaryotic microorganisms.

BACKGROUND

Several methods are known from the state of the art for detection and identification of microorganisms. Optical methods are particularly popular amongst the various detection methods due to their high speed and the low preparation efforts they require.

One way to detect and identify microorganisms is based on the evaluation of inelastically scattered light from the specimen. This so-called Raman scattering can be used to detect but also to identify substances, molecules and the like based on their specific Raman spectrum. The Raman spectrum is achieved by spectrally resolving the inelastically scattered light from the sample. Thereafter, the measured spectrum is evaluated by matching it with the Raman spectra of known substances or microorganisms.

In comparison to fluorescence-based detection, Raman-spectroscopic detection has the advantage that no labelling of the sample is required and that the specificity of the Raman spectra associated to the various microorganisms is more pronounced than the specificity of the associated (auto-) fluorescence spectra.

As the Raman signal is usually orders of magnitude smaller than a fluorescence signal and as almost biological samples exhibit some degree of luminescence, such as for example fluorescence, the detection and separation of the Raman signal is comparably demanding. Also, maintaining a sufficiently good signal quality in Raman spectroscopic measurements becomes even more difficult when the amount of the sample is small.

In order to increase the signal-to-noise ratio of a Raman measurement, a first measure is to increase the illumination power of the illumination source, e.g. the laser. However, when measuring biological samples the amount of energy deposited on the sample during exposition to the laser light has to be limited in order not to affect or deteriorate the sample.

Another way to increase the signal-to-noise ratio for microscopic measurements is to perform these measurements using a so-called confocal detection scheme.

In such confocal microscopic Raman-spectroscopic measurements, the detection limit can be pushed to smaller amounts of sample. Also, the tighter the excitation light is focused on the sample, the stronger and more restrictive the confocality can be chosen and consequently the signal-to noise ratio is increased even more.

However, as these measurements with a tightly focused excitation light require high numerical aperture objective lenses, the working distances of these microscopes is strongly reduced, such that the objective lens and the sample have to be arranged in very close proximity. The working distance for example of a 100× oil immersion objective lens with a numerical aperture of 1.4 lies in the sub-millimeter range.

Furthermore, as the optics of such objective lenses are rather complex, refractive index changes in the light path will lead to aberrations of the focused laser light. Plastic covers of the sample chamber, air or other materials for example will cause such refractive index changes. Optical aberrations in turn always lead to an increased focal volume and thus to a deteriorated signal-to noise ratio.

However, in many potential applications, sterility conditions have to be met. Contamination of the sample by the environment or contamination of the environment by the sample is to be avoided. Thus, the use of a closed sample chamber or a sample chamber comprising a lid is mandatory. Furthermore, as biological samples are often grown in Petri dishes or contact plates that contain nutrition medium or a nutrition gel on the bottom, it is impossible to optically access the sample from the bottom of such a dish or plate, while maintaining a sufficiently good signal quality.

One solution to the problem is to house the whole confocal systems inside a closed atmosphere in order to avoid contamination of the sample.

Such housed systems however are comparably expensive and elaborate to handle.

SUMMARY

Therefore, the problem underlying the present invention is to provide a system, and a method allowing the measurement of Raman-spectroscopic spectra of biological samples while keeping the sample in a separate atmosphere.

This problem is solved by a system having the features of claim 1, and a method having the features of claim 14.

Preferred embodiments are stated in the sub claims and the description.

BRIEF DESCRIPTION OF THE DRAWINGS

Further features and advantages of the invention shall be described by means of a detailed description of embodiments with reference to the Figures, wherein it is shown in FIG. 1 a schematic setup of a system according to the invention.

DETAILED DESCRIPTION

Figure 1:
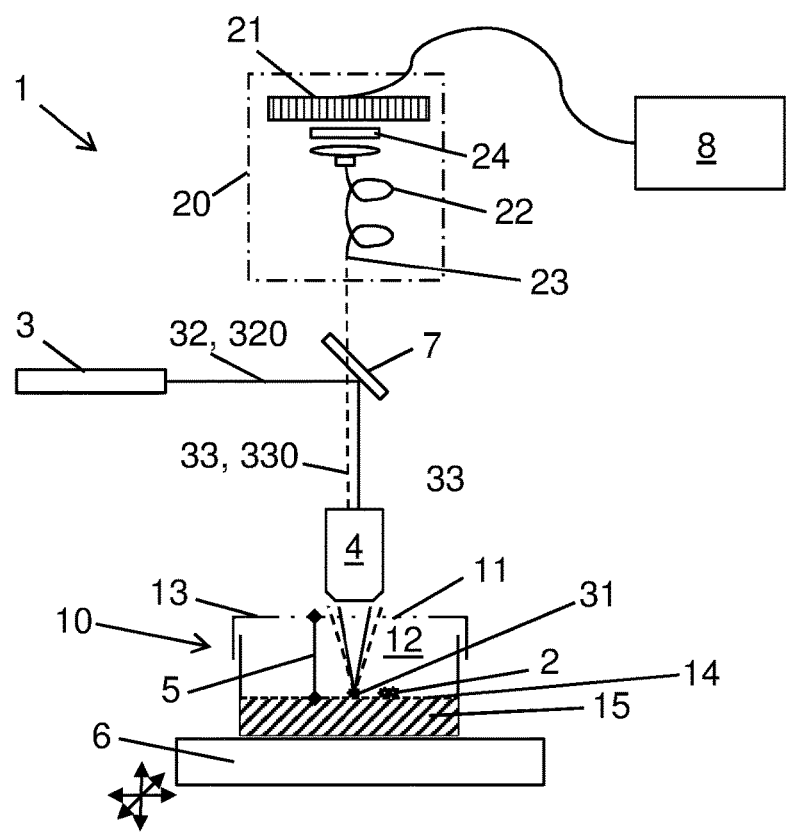

According to claim 1, a system for confocal Raman-spectroscopic measurements for biological samples, comprises at least the following components:

- a sample chamber, wherein said sample chamber is configured to house a sample in a closed or closable chamber volume of the sample chamber,
- an excitation light source, such as for example a laser or a lamp,
- an objective lens, such as for example a long-working-distance objective, configured to focus excitation light of the excitation light source through a massive, i.e. consisting of a solid material, ceiling portion of the sample chamber into a focal volume in the chamber volume and to collect inelastically scattered light stemming from the focal volume, a confocal detection arrangement that is particularly arranged confocally with respect to the excitation focal volume, comprising means for a confocal detection of a Raman signal comprised in the inelastically scattered light from the focal volume, particularly from an overlapping detection volume, and a detector that is configured to detect and to record said Raman signal, wherein the distance between particularly an outer side of the ceiling portion of the sample chamber and the focal volume is greater than one millimeter during operation of the system.

The system according to the invention provides advantageously a high signal-to-noise ratio for Raman-spectroscopic measurements of biological samples, while due to the increased distance between objective lens and the sample in the sample chamber, measurements can be performed under a separated atmosphere.

As particularly biological samples are often grown on a bottom of the sample chamber on top of nutrition gels, culture- or nutrient media or the like, the advantage of this system is that the arrangement of the objective lens is chosen such that the system enables measurements through the ceiling portion of the sample chamber, such that nutrition gels, or pads are no hindrance for the high signal-to-noise confocal Raman measurements.

One challenge that is overcome by the invention is the provision of a sufficiently high working distance between the objective lens and the sample, such that the presence of a lid of the sample chamber is not impeding the measurement due to its distance to the sample.

Furthermore, the system according to the invention surprisingly provides a comparably high signal-to-noise ratio even though optically the focal volume might be distorted by aberrations induced for example by a lid of the sample chamber or gas between then sample and the objective lens.

The focal volume can be described by the spatial intensity distribution of the excitation light and is particularly defined by the volume that comprises excitation intensities that are greater than $1e^{-2}$ times the maximum intensity value that usually lies in the centre of the focal volume.

The detection volume on the other hand can be defined by the spatial detection probability, wherein the detection volume can for example be defined as the volume in which the photon detection probability is greater then $1e^{-2}$, if one assumes a detection efficiency of 1 in the centre of the detection volume. The combination of the focal volume, that can be understood as an excitation or scattering probability, and the detection volume, that is also given by the position of the confocal pinhole, describes the overall detection probability of the system, if detection efficiencies of the detectors, absorption processes and the like are neglected.

The system according of the invention therefore uniquely combines features for a robust and simultaneously sensitive measurement.

According to another embodiment of the invention, the sample chamber comprises a bottom portion surrounded by a chamber wall, wherein the bottom portion is an entirely even surface arranged at a fixed distance to the ceiling portion, wherein the bottom portion is furthermore configured and arranged for cultivation of biological samples.

According to another embodiment of the invention, the distance between the ceiling portion of the sample chamber and the focal volume is greater than 3 mm, particularly greater than 5 mm, more particularly greater than 9 mm during a measurement.

While the distance between the sample chamber and the focal volume according to the invention is characterised by a lower limit, it is noted that an upper limit of working distances lies for example by distance greater than 1 m.

The increased distance between the ceiling portion and the focal volume require increased working distances of the objective lens, such that the system becomes more and more elaborate to conceive.

According to another embodiment of the invention, the objective lens comprises a numerical aperture equal to or greater than 0.5, particularly greater than 0.55, more particularly equal to or greater than 0.6.

The higher the numerical aperture, the higher the degree of focusing can be achieved and the greater the collection angle for the scattered light becomes. On the other hand, optical aberrations from distortions in the light path become relatively more relevant for high apertures, so that the choice of the numerical aperture needs to balance different technical aspects.

According to another embodiment of the invention, an intended widening of the excitation focus of the laser light beam allows to excite the sample with a higher power without affecting its structural properties. Thus, a higher signal can be fed into the adapted diameter of the fibre and a higher Raman signal can be achieved.

Due to the potential optical aberrations—increasing the focal volume—induced by the transparent ceiling portion of the sample chamber, it advantageously becomes possible to excite the sample with higher illumination power without affecting its structural or biological properties. Thus, a higher signal can for example be fed into the adapted diameter of the optical fibre of the detection arrangement and a higher Raman signal can be achieved.

According to another embodiment of the invention, the objective lens is a long-working-distance objective with a working distance of at least 4 mm, particularly more than 9 mm, more particularly more than 10 mm.

Such long working distance objective lenses are particularly advantageous for measurements through the ceiling portion.

According to another embodiment of the invention the objective lens has a magnification of 50× and a working distance of 11 mm.

According to another embodiment of the invention, the relay lens has a focal length 14 mm of an and numerical aperture of 0.22.

The relay lens is the lens that is used to focus the particularly collimated light from the objective lens on the pinhole. According to another embodiment of the invention, the system is configured to confocally measure Raman signals, particularly a Raman spectrum of biological specimens such as for example microbiological specimens, such as for example microorganisms, microbes, bacteria, biofilms, and/or microbe colonies that are particular grown on a nutrition gel or in a fluid nutrition medium.

According to another embodiment of the invention, the sample chamber is sealed air-tightly, wherein the chamber might particularly be designed such that it provides an opening for the provision of an air or gas flow with an external air or gas flow system, such that the chamber is still part of an air-tight system.

Further, the sample chamber might comprise another opening configured for the provision of nutrition media for the microorganisms.

Such kind of sample chamber, which may comprise openings for nutrition and atmosphere maintenance while keeping the sample separated from the surrounding atmosphere, provides an advantageous way of growing and measuring the biological sample without the need to relocate the sample to a dedicated measurement chamber for the measurement procedure.

According to another embodiment of the invention, the sample chamber comprises gas or air between the ceiling portion of the sample chamber and the focal volume during operation.

As mentioned above, such a configuration is particularly challenging for confocal Raman spectroscopic measurements through a ceiling portion, as the refractive index changes from the ceiling portion material to gas or air are comparably large, such that the optics of the system have to be adjusted to strong aberrational effects.

Furthermore, like in the case of contact plates configured for the growth of microorganisms, the sample chamber might comprise a liquid such that between the ceiling portion and the liquid, the gas or air layer is comprised. Here, even more refractive index changes are present such that the focal volume will experience dramatic optical aberrations, while nonetheless the system according to the invention remains operational.

According to another embodiment of the invention, the ceiling portion of the sample chamber has a thickness of more than 0.5 mm, particularly more than 0.75 mm or more than 0.9 mm.

This embodiment advantageously allows the use of cost-efficient state of the art sample chambers that are not necessarily manufactured for Raman-spectroscopic measurements of biological samples through the ceiling portion. These sample chambers often exhibit ceiling portions that are thicker than 0.5 mm and are for example solely specifically designed for the growth and maintenance of biological samples or bacterial cultures—but not for their measurement.

The sample chamber is preferably removably arrangeable on a sample stage of the system.

According to another embodiment of the invention, the ceiling portion of the sample chamber comprises portions of different optical path lengths, e.g. due to varying thickness and/or wherein the ceiling portion of the sample chamber comprises portions of different optical transparency, wherein the optical path lengths and/or the optical transparency of the said portions vary within 10% of a mean optical path lengths value and/or mean transparency value.

According to another embodiment of the invention, the variation of optical path length or optical transparency around a mean optical path length or a mean optical transparency respectively in the ceiling portion is greater than 1%, 2% or 5%. As many low-cost sample chambers that are not specifically made for microscopic purposes exhibit such variations in their optical properties, the system according to the invention advantageously provides the possibility to use such low-cost sample chambers.

According to another embodiment of the invention, at least the ceiling portion of the sample chamber comprises a transparent material such as for example a transparent polymer, glass, zirconia, sapphire, diamond and/or quartz.

Transparent in this regard refers to a spectral transparency that might be limited to the wavelength of the excitation light and the inelastically scattered light from the sample. Thus, the transparency of the ceiling portion does not necessarily need to extend over the whole ultra-violet, visible and/or infrared spectrum, but might comprise only a portion of it.

According to another embodiment of the invention, the ceiling portion is comprised in a lid of the sample chamber, wherein said lid can be opened and closed such that the volume comprised by the sample chamber can be opened or closed, wherein the sample chamber is further configured to keep a gas volume inside the chamber volume separated from the atmosphere outside of the sample chamber, when the lid is closed, such that for example microorganisms that are intended to be present inside the sample chamber are kept inside the chamber volume, while perturbing microorganisms and/or biological active substances are kept outside of the chamber.

The sample chamber according to this embodiment is particularly configured that it maintains potential sterility requirements of a certified clean environment.

Such biological active substances comprise for example, viruses, bacterial phages, bacteria, and/or other molecules that might compromise or alter the biological functions of the sample.

According to another embodiment of the invention, the system comprises a scanning system that is configured to scan the focal volume to different positions, over an area or through a volume within the sample chamber.

The scanning system can comprise for example a beam scanning device and/or a stage-scanning device.

Beam scanning techniques allow a more flexible layout of the sample holder, wherein the stage scanning technique provides a more accurate way of scanning the focal volume through the sample.

According to another embodiment of the invention, the sample chamber is a Petri dish or a contact plate with a lid comprising the ceiling portion.

This kind of sample chamber advantageously provide the option to grow the microorganisms and colonies on a nutrition gel, wherein the bottom of the sample chamber might comprise a semi-permeable film on which the bacteria grow and wherein between the bottom and the film the nutrition gel is comprised. Such configurations are common in the state of the art and are manufactured comparably cost-efficient.

According to another embodiment of the invention, the system is configured to detect and classify Raman-signatures of microbe colonies comprising less than ten or eight microbes. According to another embodiment of the invention, the system is configured as an epi-illumination system.

An epi-illumination system is particularly more robust in its alignment/misalignment behaviour than systems comprising an objective lens and a condenser lens that are arranged on opposite sides of the sample/sample chamber.

According to another embodiment of the invention, the system comprises a computer that is configured to process and to compare a recorded Raman spectrum to a plurality of Raman spectra or associated data that are stored in a database.

A computer is a device or system, that particularly comprises a microprocessor that is programmable and that is configured to execute programming code.

According to another embodiment of the invention, the confocal detection arrangement comprises an optical fibre, wherein said optical fibre is particularly a multi-mode optical fibre, wherein said optical fibre is configured and arranged as a confocal pinhole of the confocal detection arrangement, particularly wherein the diameter of the optical fibre is greater than or equal to 25 μm, particularly equal to 50 μm, 60 μm or 75 μm.

This embodiment provides the system with a variable, comparably weak confocality that is tolerant to aberrations and comparably large focal volumes, e.g. due to the long working distance/low numerical aperture.

According to another embodiment of the invention, the objective lens, the excitation light source, and the confocal detection arrangement are comprised by a microscope.

The problem according to the invention is also solved by a method for measuring a Raman signal from a sample, particularly with a system according to the invention, comprising the steps of
- arranging a sample housed in a closed sample chamber at a distance of at least 1 mm, particularly 3 mm, 5 mm, 9 mm away from an objective lens, wherein a massive, transparent ceiling portion of the sample chamber is arranged between the sample and the objective lens,
- illuminating the sample through the objective lens and the ceiling portion of the sample chamber with excitation light, wherein the excitation light is focused within a focal volume onto or into the sample,
- confocally detecting inelastically scattered light from the illuminated focal volume of the sample,
- determining a Raman spectrum of the confocally detected inelastically scattered light.

According to another embodiment of the invention the method further comprise the steps of
- particularly processing the recorded Raman spectrum and generating data associated to the Raman spectrum,
- comparing the estimated Raman spectrum with a plurality of Raman spectra stored in a database and/or,
- comparing the associated data from the estimated Raman spectrum with data associated to a plurality of Raman spectra stored in a database.

FIG. 1 shows a system 1 according to the invention comprising an objective lens 4, a laser as an excitation light source 3 and a confocal detection arrangement 20. Wherein the confocal detection arrangement 20 comprises an optical multi-mode fibre 22 with a diameter of 25 μm. One end of the fibre 22 is arranged such that it acts as a pinhole 23 for the confocal detection, wherein the other end is arranged such that a spectrometer 21—in this example a spectrograph and a sensitive electron-multiplying CCD-device—can record a Raman spectrum. A suitable filter 24 is arranged in front of the spectrometer 21 that filters out interfering light contributions from the sample 2 or other components such as the lid 13 of the sample chamber 10 as well as the excitation light 32. The light 32 from the excitation light source 3 is focused with the objective lens 4 through a ceiling portion 11 of the sample chamber 10 into the sample chamber 10 and the biological sample 2 and the inelastically scattered light 33 from the sample 2 is subsequently collected by the same objective lens 4. The excitation light 32 from the laser 4 in this example comprises a centre wavelength of 532 nm, and thus the fraction of the scattered light 33, which encompasses the relevant signal in this embodiment of the invention, comprises wavelengths of more than 532 nm. As lasers 4 are particularly exhibiting monochromatic emission properties, the variation around the centre wavelength is usually less than 10 nm. It is noted that other wavelengths for the excitation (and thus also for scattered light detection) can be used as well. The distance 5 between the lid 13 of the sample chamber 10 and the sample 2 is greater than 7 mm in this example. Therefore the distance 51 (see FIG. 2, right panel) between the objective lens 4 and focal volume 31 that is placed on or in the sample 2 during operation of the system 1 is at least equally large or larger. This finding applies to all embodiments of the invention. A dichroic beam splitter 7 separates the detection light path (depicted as a broken line 330), i.e., the scattered light 33, from the excitation light path (depicted as a solid line 320), i.e. the excitation light 32. After passing the dichroic beam splitter 7 the scattered light 33 is focused on the pinhole end 23 of the optical fibre 22 such that out-of-focus signals are strongly diminished. In this example, a long-working-distance objective 4 is used for focusing the excitation light 33 and collecting the scattered light 32 in order to account for the distance of the chamber lid 13 of the sample chamber 10 and the sample 2. The objective lens 4 comprises a numerical aperture of 0.6.

The sample chamber 10 comprises a removable chamber lid 13 that is made from a transparent polymer such that the ceiling portion 11 comprised by the chamber lid 13 is transparent for the excitation light 32 and the inelastically scattered light 33. The sample 2 is located on a semipermeable membrane 14 under which a nutrition gel 15 is located.

The sample chamber 10 is located on a scanning unit 6 that is configured to move the sample chamber 10 along three dimensions (x, y, z depicted by the three arrows), such that the focal volume 31 can be placed at different positions within the sample chamber 10 and thus on different positions of the sample 2.

A computer 8 is configured to receive the recorded signals of the spectrometer 21 and to process the recorded Raman spectra. Furthermore the computer 8 is configured to compare the recorded and processed Raman spectra with Raman spectra or associated data stored in a database comprising a plurality of Raman spectra and/or their associated data such as to identify the sample 2 in the sample chamber 10.

Figure 2:
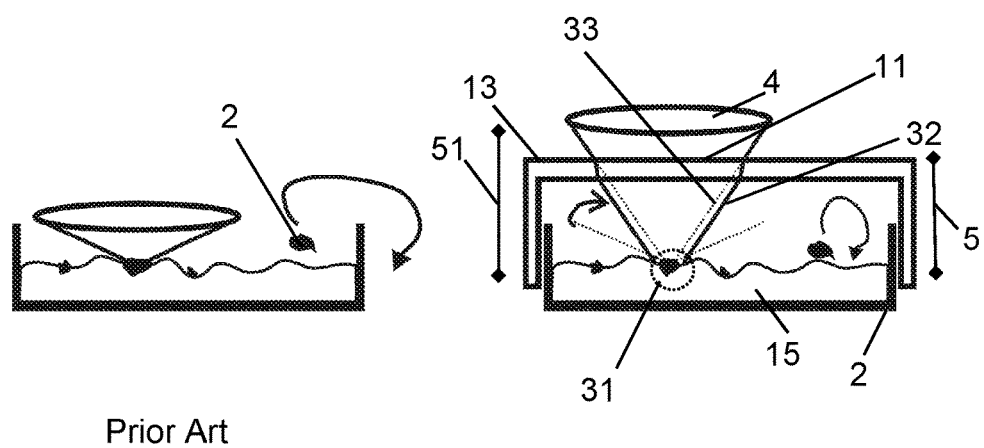
FIG. 2 a schematic drawing of the effect of the ceiling portion on the focal volume and the optical path in comparison to state of the art systems.

In FIG. 2, left panel, a system according to the state of the art, where the presence of a lid is not feasible during measurement, due to the following reasons. The optical aberrations a lid would introduce into the optics of the system would compromise the performance of the system of the state of the art. Furthermore a too short working distance of the objective lens renders the introduction of a lid between the sample and the objective lens impossible.

FIG. 2, right panel, shows a system according to the invention, where aberrations induced by the presence of the lid 13 on the sample chamber 10 are accounted for by the layout of the other components of the system. In order to account for these aberrations a long working distance objective lens 4, such as for example an objective lens comprising a working distance of 11 mm and a numerical aperture of 0.6 is used that enables the measurement at first place. Furthermore, the comparably large focal volume 31, partly due to aberrations partly due to the lower numerical aperture of the long-working-distance objective, is accounted for by providing a comparably large pinhole diameter of 25 μm given by the optical fibre 22.

Alternatively an objective with a working distance of 9.8 mm and a numerical aperture of 0.55 can be used as well.

We claim:

1. System (1) for confocal Raman-spectroscopic measurements, comprising at least the following components:
   a sample chamber (10), wherein said sample chamber (10) is configured to house a sample (2) in a closed chamber volume (12) of the sample chamber (10), wherein the sample chamber (10) comprises a ceiling portion (11), wherein the ceiling portion (11) is comprised in a lid (13) of the sample chamber (10), wherein said lid (13) can be opened and closed such that the chamber volume (12) comprised by the sample chamber (10) can be opened or closed, wherein the sample chamber (10) is further configured to keep a gas volume inside the chamber volume (12) separated from the atmosphere outside of the sample chamber (10), when the lid (13) is closed,
   an excitation light source (3), an objective lens (4), configured to focus excitation light (32) of the excitation light source (3) through the ceiling portion (11) of the sample chamber (10) in a focal volume (31) in the chamber volume (12) and to collect inelastically scattered light (33) stemming from the focal volume (31), wherein the objective lens comprises a numerical aperture of at least 0.55, a confocal detection arrangement (20), comprising a confocal pinhole (23) or an optical fibre configured and arranged as a confocal pinhole (23) for confocal detection (22, 23) of a Raman signal comprised in the inelastically scattered light (33) from the focal volume (31), and a detector (21) that is configured to detect and to record said Raman signal, wherein the objective lens focuses the excitation light through the ceiling portion and the distance (5) between the ceiling portion (11) of the sample chamber (10) and the focal volume (31) is greater than three millimeters during operation of the system (1).

2. System according to claim 1, characterized in that the distance (5) between the ceiling portion (11) of the sample chamber (10) and the focal volume (31) is greater than 9 mm during operation of the system (1).

3. System according to claim 1, wherein the system (1) is configured to measure Raman signals of biological specimens (2).

4. System according to claim 1, characterized in that the sample chamber (10) comprises air or other gas between the ceiling portion (11) of the sample chamber (10) and the focal volume (31) during operation.

5. System according to claim 1, wherein the ceiling portion (11) of the sample chamber (10) has a thickness of more than 0.5 mm.

6. System according to claim 1, wherein the ceiling portion (11) of the sample chamber (10) comprises portions of different optical path lengths and/or wherein the ceiling portion (11) of the sample chamber (10) comprises portions of different optical transparency, wherein the optical path lengths and/or the optical transparency of the said portions varies within 10% of a mean optical path lengths value and/or mean transparency value.

7. System according to claim 1, wherein at least the ceiling portion (11) of the sample chamber (10) comprises a transparent material.

8. System according to claim 1, characterized in that the system (1) comprises a scanning unit (6) that is configured to scan the focal volume (31) to different positions, over an area or through a volume within the sample chamber (10).

9. System according to claim 1, wherein the sample chamber (10) is a Petri dish or a contact plate with a lid (13) comprising the ceiling portion (11).

10. System according to claim 1, wherein the system (1) is configured as an epi-illumination system.

11. System according to claim 1, wherein the system comprises a computer (7) that is configured to process and to compare a recorded Raman spectrum to a plurality of Raman spectra or associated data that are stored in a database.

12. System according to claim 1, wherein said optical fibre (22) is a multi-mode optical fibre, wherein the diameter of the optical fibre (22) is greater than or equal to 25 µm.

13. Method for measuring a Raman signal from a sample (2), particularly with a system (1) according to claim 1, comprising the steps of arranging a sample (2) housed in a closed sample chamber (10) at a distance (5) of at least 3 mm, 5 mm or 9 mm away from an objective lens (4), wherein a ceiling portion (11) of the sample chamber (10) is comprised in a lid (13) and wherein the ceiling portion (11) is arranged between the sample (2) and the objective lens (4), wherein said lid (13) can be opened and closed such that the chamber volume (12) comprised by the sample chamber (10) can be opened or closed, wherein the sample chamber (10) is further configured to keep a gas volume inside the chamber volume (12) separated from the atmosphere outside of the sample chamber (10), when the lid (13) is closed;

illuminating the sample (2) through the objective lens (4) and the ceiling portion (11) of the sample chamber (10) with excitation light (32), wherein the excitation light (32) is focused into a focal volume (31) onto or into the sample (2), confocally detecting inelastically scattered light (33) from the illuminated focal volume (31) of the sample (2), determining a Raman spectrum of the confocally detected inelastically scattered light (33).

14. Method according to claim 13, wherein the method further comprises at least the steps of comparing the determined Raman spectrum with a plurality of Raman spectra stored in a database and/or, comparing the associated data from the determined Raman spectrum with data associated to a plurality of Raman spectra stored in a database.

* * * * *